United States Patent
Brenneman et al.

(10) Patent No.: US 8,641,724 B2
(45) Date of Patent: Feb. 4, 2014

(54) DEVICES, SYSTEMS AND METHODS FOR CREATION OF A PERIPHERALLY LOCATED FISTULA

(75) Inventors: Rodney Brenneman, San Juan Capistrano, CA (US); Dean A. Schaefer, Aliso Viejo, CA (US); J. Christopher Flaherty, Topsfield, MA (US)

(73) Assignee: Rox Medical, Inc., San Clemente, CA (US)

( * ) Notice: Subject to any disclaimer, the term of this patent is extended or adjusted under 35 U.S.C. 154(b) by 939 days.

(21) Appl. No.: 11/946,454

(22) Filed: Nov. 28, 2007

(65) Prior Publication Data
US 2008/0119879 A1    May 22, 2008

Related U.S. Application Data

(63) Continuation of application No. PCT/US2006/024858, filed on Jun. 26, 2006.

(60) Provisional application No. 60/696,319, filed on Jun. 30, 2005.

(51) Int. Cl.
*A61F 11/00*    (2006.01)

(52) U.S. Cl.
USPC .................... 606/108; 606/194; 606/153

(58) Field of Classification Search
USPC .............. 606/153, 108; 600/16–18, 464, 465, 600/466, 467, 468–471; 604/8, 96.01; 623/1.11, 23.7, 1.15
See application file for complete search history.

(56) References Cited

U.S. PATENT DOCUMENTS

| | | | | |
|---|---|---|---|---|
| 4,739,762 A | * | 4/1988 | Palmaz | 623/1.11 |
| 4,776,337 A | * | 10/1988 | Palmaz | 623/1.11 |
| 4,950,227 A | * | 8/1990 | Savin et al. | 623/1.12 |
| 5,026,377 A | * | 6/1991 | Burton et al. | 606/108 |
| 5,201,757 A | * | 4/1993 | Heyn et al. | 606/198 |
| 5,445,646 A | * | 8/1995 | Euteneuer et al. | 606/198 |

(Continued)

FOREIGN PATENT DOCUMENTS

| | | |
|---|---|---|
| WO | WO 97/27898 A1 | 8/1997 |
| WO | WO 02/15796 A2 | 2/2002 |
| WO | WO 2004/091696 A1 | 10/2004 |

OTHER PUBLICATIONS

International Search Report of PCT Application No. PCT/US2006/024858, dated Nov. 2, 2006, 1 page only.

(Continued)

*Primary Examiner* — Corrine M McDermott
*Assistant Examiner* — Son Dang
(74) *Attorney, Agent, or Firm* — Wilson, Sonsini, Goodrich & Rosati (57) ABSTRACT

Devices, systems and methods are disclosed for the formation of an arteriovenous fistula in the limb of the patient. Embodiments include a device for the creation, modification and maintenance of a fistula that includes an integral fistula creation assembly near its distal end that passes through the skin of the patient, through a first vessel such as an artery, and into a second vessel such as a vein. The fistula creation assembly preferably includes an anastomotic implant that is placed within the fistula to maintain long-term blood flow therethrough. The devices, systems and methods can be used to treat patients with one or more numerous ailments including chronic obstructive pulmonary disease, congestive heart failure, hypertension, hypotension, respiratory failure, pulmonary arterial hypertension, lung fibrosis and adult respiratory distress syndrome.

16 Claims, 6 Drawing Sheets

(56) References Cited

U.S. PATENT DOCUMENTS

| | | | |
|---|---|---|---|
| 5,743,874 A * | 4/1998 | Fischell et al. | 604/103.1 |
| 5,830,222 A * | 11/1998 | Makower | 606/159 |
| 5,830,224 A * | 11/1998 | Cohn et al. | 606/167 |
| 5,843,090 A * | 12/1998 | Schuetz | 623/1.11 |
| 5,951,569 A * | 9/1999 | Tuckey et al. | 606/108 |
| 5,989,280 A * | 11/1999 | Euteneuer et al. | 623/1.1 |
| 6,042,589 A * | 3/2000 | Marianne | 606/108 |
| 6,081,738 A * | 6/2000 | Hinohara et al. | 600/407 |
| 6,231,587 B1 * | 5/2001 | Makower | 606/198 |
| 6,280,412 B1 * | 8/2001 | Pederson et al. | 604/103.07 |
| 6,283,951 B1 * | 9/2001 | Flaherty et al. | 604/529 |
| 6,290,728 B1 * | 9/2001 | Phelps et al. | 623/23.7 |
| 6,409,751 B1 * | 6/2002 | Hall et al. | 623/1.11 |
| 6,579,311 B1 * | 6/2003 | Makower | 623/1.23 |
| 6,692,482 B2 * | 2/2004 | Heller et al. | 604/528 |
| 6,709,444 B1 * | 3/2004 | Makower | 606/198 |
| 6,746,464 B1 * | 6/2004 | Makower | 606/185 |
| 6,926,690 B2 * | 8/2005 | Renati | 604/8 |
| 7,235,095 B2 * | 6/2007 | Haverkost et al. | 623/1.12 |
| 7,331,985 B2 * | 2/2008 | Thompson et al. | 623/1.11 |
| 7,335,220 B2 * | 2/2008 | Khosravi et al. | 606/213 |
| 7,744,621 B2 * | 6/2010 | Paul et al. | 606/195 |
| 2001/0016753 A1 * | 8/2001 | Caprio et al. | 606/192 |
| 2001/0037141 A1 * | 11/2001 | Yee et al. | 623/1.11 |
| 2002/0002349 A1 * | 1/2002 | Flaherty et al. | 604/164.11 |
| 2002/0049486 A1 * | 4/2002 | Knudson et al. | 623/1.1 |
| 2003/0158509 A1 * | 8/2003 | Tweden et al. | 604/8 |
| 2004/0098105 A1 * | 5/2004 | Stinson et al. | 623/1.15 |
| 2006/0024359 A1 * | 2/2006 | Walker et al. | 424/450 |
| 2006/0161197 A1 * | 7/2006 | Paul et al. | 606/195 |
| 2007/0049970 A1 * | 3/2007 | Belef et al. | 606/232 |

OTHER PUBLICATIONS

International Preliminary Report on Patentability, issued Jan. 9, 2008, 5 pages total.

European search report and opinion dated May 15, 2013 for EP Application No. 06774036.5.

* cited by examiner

Fig. 4b

DEVICES, SYSTEMS AND METHODS FOR CREATION OF A PERIPHERALLY LOCATED FISTULA

CROSS-REFERENCES TO RELATED APPLICATIONS

This application is a continuation of PCT/US2006/024858, filed on Jun. 26, 2006, which claims priority from U.S. Application No. 60/696,319, filed on Jun. 30, 2005, the full disclosures of each which are incorporated herein by reference.

BACKGROUND OF THE INVENTION

Field of the Invention

The present invention relates generally to medical devices and methods. More particularly, the present invention relates to devices and methods for creating or modifying a fistula between a first vessel and a second vessel, such as for the treatment of chronic obstructive pulmonary disease.

Chronic obstructive pulmonary disease affects millions of patients in the United States alone. The present standard of care is externally supplied oxygen therapy, which requires a patient to remain near a stationary oxygen source or carry a bulky oxygen source when away from home or a treatment facility. It is easy to appreciate that such oxygen therapy has many disadvantages.

Lung reduction surgery has recently been proposed for treating patients with chronic pulmonary disease. Such surgery, however, is not a panacea. It can be used on only a small percentage of the total patient population, requires long recovery times, and does not always provide a clear patient benefit. Even when successful, patients often continue to require supplemental oxygen therapy.

There is therefore a need for improved approaches, including both devices and methods, for treating patients suffering from chronic obstructive pulmonary disease. If would be desirable if such devices and methods were also useful for treating patients with other conditions, such as congestive heart failure, hypertension, lung fibrosis, adult respiratory distress syndrome, and the like. Such devices and methods should provide for effective therapy, preferably eliminating the need for supplemental oxygen therapy in the treatment of chronic obstructive pulmonary disease. There is a need for simplified devices and procedural methods that reduce costs to the patient and healthcare system, as well as decrease procedure times and minimize patient risks. Improved devices and procedures must be developed to apply to a broad base of patient populations with a wide range of applicable arteriovenous anatomies. At least some of these objectives will be met by the invention described hereinafter.

BRIEF SUMMARY OF THE INVENTION

According to a first aspect of the invention, a device for creating a fistula in a patient is disclosed. The device comprises an elongate tubular structure comprising a proximal end and a distal end. The distal end is configured to penetrate or otherwise pass first through the skin of the patient, then through a first vessel, and then into a second vessel. The device includes an integral assembly configured to create a fistula between two neighboring vessels. In a preferred embodiment, the first vessel is an artery and the second vessel is a vein. In an alternative, also preferred embodiment, the first vessel is a vein and the second vessel is an artery. The fistula is typically created at a location wherein the artery and vein vessel walls are within 20 mm of each other. The fistula is created to provide therapeutic benefit, such as for an acute period less than twenty-four hours, a sub-chronic period between twenty-four hours and thirty days, or for a chronic period greater than thirty days. The fistula creation assembly is preferably mounted on a core that is slidable within an outer sheath of the device. The fistula creation assembly can be uncovered from the sheath by an operator through advancement of the core, retraction of the sheath, or a combination of the two movements. In a preferred embodiment, a second slidable core, such as a slidable needle assembly with a sharpened, beveled tip, is slidingly received by the first core. When fully advanced, the needle assembly exits the distal end of both the sheath and the first core, and assists in penetrating first through the skin of the patient and then through the tissue that exists along the trajectory to the proposed fistula. Both the first core and the sheath preferably have tapered ends to assist in penetration and/or advancement through the skin and tissue up to the fistula site. In another preferred embodiment, the needle assembly includes a guidewire lumen for insertion of a guidewire from outside the patient's body, through the first vessel and into the lumen of the second vessel. In another embodiment, the needle assembly is removable. In a preferred embodiment, the device is rigid along a majority of its length. In an alternative embodiment, the device is flexible along a majority of its length, such as a flexible section that can be advanced down a segment of the first vessel prior to entering the second vessel. In another alternative embodiment, the device includes both flexible segments and rigid segments along its length.

The fistula creation assembly of the present invention can be configured in numerous forms to produce the desired fistula. In a preferred embodiment, a cone shaped dilator is expanded and/or delivers energy to create the fistula. In another embodiment, an expandable balloon is used to create the fistula. An anastomotic implant is preferably deployed to initially create the fistula and/or to improve the long-term patency of the fistula. The implant can perform numerous functions, and may include self-expanding materials, plastically deformable materials, or a combination of self-expanding or plastically deformable materials. In a preferred embodiment, the anastomotic implant forms the fistula into an oval cross section. In an alternative embodiment, the anastomotic implant forms the fistula into a circular cross section. Numerous forms of energy can be used to create and/or improve the fistula, including energies selected from the group consisting of: electrical energy such as radiofrequency or microwave energy; cryogenic energy; heat; radiation; chemical energy; light such as light delivered to photoreactive agents; and combinations thereof. The fistula creation assembly may deliver an agent to the fistula and its surrounding tissue, such agents selected from the group consisting of: anti-proliferative; anti-biotic; anti-thrombogenic; and combinations thereof.

In a preferred embodiment, the device is configured to create a fistula to treat a patient suffering from COPD, such as via the fistula decreasing systemic vascular resistance of the patient. In these and other patient populations, the fistula may provide therapy by increasing the oxygen content of venous blood, such as blood supplied to a lung of the patient. The fistula may additionally cause oxygen content in arterial blood to also increase. The fistulas of the present invention are configured to have blood flow through the fistula of at least 5 ml/min, and preferably greater than 50 ml/min.

In yet another preferred embodiment, the device includes a handle at its proximal end. The handle includes one or more controls, such as controls to advance and/or retract a slidable core. In a preferred embodiment, one or more controls are included to perform a function selected from the group consisting of: initiate or modify the delivery of energy to an intended or existing fistula location; expand a distal portion of the device such as an expandable dilator or inflatable balloon; deploy an implant such as an anastomotic device which applies tension between the two vessels at the fistula location and/or scaffolds the lumen of the fistula; and combinations thereof.

In yet another preferred embodiment, the device is configured to create a fistula in a limb of a patient, such as between an artery and vein selected from the group consisting of: axillary artery; brachial artery; ulnar artery; radial artery; profundal artery; femoral artery; iliac artery; popliteal artery; carotid artery; saphenous vein; femoral vein; iliac vein; popliteal vein; brachial vein; basilic vein; cephalic vein; medial forearm vein; medial cubital vein; axillary vein; and jugular vein. In an alternative embodiment, the fistula is located in the abdomen or thorax of the patient.

In yet another preferred embodiment, the fistula creation device further comprises a flow measurement element, such as an ultrasound or Doppler ultrasound element, or a lumen that allows a flow measurement catheter to be inserted into the proximal end of the device and advanced to a location near or beyond the device's distal end. Flow measurement can be made directly using Doppler technologies and techniques, or indirectly by measuring flow channel geometries.

In yet another preferred embodiment, the fistula creation device further comprises flow adjustment means mounted to one or more of the outer sheath or an inner core. The flow adjustment means can be activated on demand by an operator and preferably includes: an energy delivery element; an agent delivery element; an inflatable balloon; an expandable dilator; a deployable implant such as a second implant of the fistula creation device; and combinations thereof.

According to a second aspect of the invention, a system for creating a fistula is disclosed. The system includes one or more of the embodiments of the fistula creation device of the first aspect of the invention, and an ultrasound visualization monitor. The visualization monitor may be configured to display information received from one or more ultrasound crystals integral to the fistula creation device, or may work with separate device such as an external or internal ultrasound probe.

According to a third aspect of the invention, a system for creating a fistula is disclosed. The system includes one or more of the embodiments of the fistula creation device of the first aspect of the invention, and an apparatus selected from the group consisting of: a balloon catheter; an anastomotic implant deployment catheter; a flow measurement device such as a flow catheter or an external Doppler probe; an angiography catheter; a venography catheter; a guidewire; an introducer; a needle; a biopsy needle; and combinations thereof. In a preferred embodiment, the system further comprises an ultrasound visualization monitor configured to provide an image received from one or more of: an ultrasound element integral to the fistula creation device; an external ultrasound probe; and an internal ultrasound apparatus such as an intravascular ultrasound catheter; and an inserted probe such as a transesophageal probe.

According to a fourth aspect of the invention, a method of creating a fistula is disclosed. The distal end of a fistula creation device is placed through the skin of the patient. The distal end, which is preferably the distal end of a sharpened, beveled tip needle assembly, such as a removable needle assembly, is advanced through a first vessel, such as a vein or an artery. The distal end is then advanced into a second vessel at an existing-fistula or an intended-fistula location. A fistula is then created, or an existing fistula is maintained, such that a long-term flow of blood is provided between the first vessel and the second vessel. The fistula creation device includes an elongate tubular structure that may be rigid along a majority of its length, may be flexible along a majority of its length, or may include rigid and flexible portions such as two rigid portions attached with a flexible hinge. In a preferred embodiment, blood flows from the first vessel to the second vessel. In an alternative, also preferred embodiment, blood flows from the second vessel to the first vessel. At the intended fistula location of the patient, the vessels may lie in various geometric configurations, such as wherein the first vessel is "on top" of the second vessel such that the lumen of the first vessel lies relatively proximate the shortest line between the lumen of the second vessel at the fistula location and the surface of the patient's skin. In alternative fistula locations, the vessels may lie in a more "side-to-side" configuration. When inserted, the elongate body of the fistula creation device is positioned to lie relatively in the plane defined by the lumens of the two vessels near the intended fistula location. While maintaining position within this plane, the fistula creation device can be inserted at an angle relatively perpendicular to the surface of the patient's skin, or at a smaller angle, such as an angle between 20 and 80 degrees. This insertion angle may be chosen by the clinician to affect the fistula angular geometry between the two vessels, such as at a small insertion angle to correspond to a similarly small angle between the lumen of the first vessel and the lumen of the fistula. Such a small angle between the first vessel lumen and the fistula lumen may be desirous to reduce turbulent flow through the fistula. In alternative embodiments, an insertion angle approximating ninety degrees may be chosen in order to minimize the length of the fistula.

In a preferred embodiment, the method further comprises the step of determining the anatomical location for the fistula. Prior to creating the fistula, the fistula location is determined using one or more of: angiography; venography; extra-vascular ultrasound; intravascular ultrasound; Doppler ultrasound; and MRI. The fistula location is determined based on an analysis of a parameter selected from the group consisting of: first vessel diameter; second vessel diameter; artery diameter; vein diameter; ratio of artery to vein diameter; distance between the artery and vein lumens; geometric relationship between the artery and vein lumens; distance from an arterial side branch; distance from an venous side branch; arterial flow; venous flow; oxygen content in artery; oxygen content in vein; wall thickness of artery; wall thickness of vein; degree of calcification of artery; degree of calcification of vein; geometric relationship between the artery and vein lumens at the fistula site; hemodynamic factors; other parameters; and combinations thereof.

In another preferred embodiment, the method further comprises the step of performing a blood flow measurement procedure, such as a procedure performed prior to fistula creation, during fistula creation, after fistula creation, and combinations thereof. The information determined during the flow measurement procedure can be used to select the fistula site, modify the fistula such as a balloon dilation fistula modification procedure and/or otherwise treat the fistula.

In yet another preferred embodiment, an anastomotic implant is placed in the fistula. The anastomotic implant is placed to provide a function selected from the group consisting of: scaffolding an opening between the first vessel and the second vessel; reducing neointimal proliferation into the fistula flow path; preventing tissue from protruding into the fistula flow path; placing a portion of the first vessel wall in tension with the tissue of the second vessel wall; reducing bleeding of the tissue neighboring the fistula; enhancing healing of the tissue neighboring the fistula; and combinations thereof. The anastomotic implant may include one or more coatings, such as anti-bacterial; anti-thrombogenic and anti-prolific coatings. The anastomotic implant may additionally or alternatively include a covered portion, such as a partial covering, such covering materials selected from the group consisting of: polytetrafluoroethylene; Dacron; Nitinol; stainless steel; and combinations thereof. The fistula creation device of the present invention preferably places the anastomotic implant.

In yet another preferred embodiment, a guidewire is placed between the first and second vessel through the fistula, prior to, during, or after the fistula is created. The guidewire preferably remains in place after the fistula creation device is removed, or partially removed, such that a second catheter device can be placed over that guidewire. The second catheter device can be used to perform a diagnostic event such as a radiographic dye injection catheter inserted to perform angiography or venography, or an ultrasound catheter used to visualize the fistula structure. The second catheter device can be used to modify the fistula such as a balloon catheter inserted to enlarge the fistula or an anastomotic implant deployment catheter inserted to increase or decrease flow through the fistula.

In yet another preferred embodiment, the fistula is created to provide therapeutic benefit that results from: a decrease is systemic vascular resistance; an increase in the oxygen content in at least a portion of the venous system such as the venous supply to a lung of the patient; and combinations thereof. Blood flow through the fistula is at least 5 ml/min and preferably greater than 50 ml/min. The fistula is preferably created between an artery and a vein at a location in a limb of the patient. The artery is selected from the group consisting of: axillary artery; brachial artery; ulnar artery; radial artery; profundal artery; femoral artery; iliac artery; popliteal artery; and carotid artery. The vein is selected from the group consisting of: saphenous; femoral; iliac; popliteal; brachial; basilic; cephalic; medial forearm; medial cubital; axillary; and jugular. The artery is preferably between 5 mm and 25 mm in diameter at the intended fistula location. The vein is preferably less than 35 mm in diameter at the intended fistula location. The fistula preferably has a non-circular or oval cross section, such that the major axis of the oval is greater than either the vein diameter or the artery diameter. In an alternative embodiment, the fistula has a circular cross section. The geometry of the cross section of the fistula is preferably matched with a similar geometry of an anastomotic implant placed during the disclosed method.

According to a fifth aspect of the invention, a kit for creating a long-term fistula in a patient for the treatment of COPD is disclosed. The kit includes a first fistula creation device for forming a fistula with a first geometry. The kit further includes a second fistula creation device for forming a fistula with a second geometry. Either the first or the second fistula creation device is used to create the long-term fistula based on an analysis of information gathered during a visualization procedure performed on the patient. The visualization procedure is preferably selected from the group consisting of: ultrasound visualization including intravascular ultrasound and extravascular ultrasound; angiography; venography; MRI; and combinations thereof. The first fistula creation device and the second fistula creation device can be configured to create a first fistula and a second fistula respectively. The first fistula and the second fistula may have two different cross sectional geometries, such as a circular and an oval cross sections, two different circular cross sections or two different oval cross sections. Varied oval cross sections may include ovals with different major axes and different minor axes, and ovals with different major axes with similar minor axes.

Both the foregoing general description and the following detailed description are exemplary and are intended to provide further explanation of the embodiments of the invention as claimed.

BRIEF DESCRIPTION OF THE DRAWINGS

The accompanying drawings, which are incorporated in and constitute a part of this specification, illustrate various embodiments of the present invention, and, together with the description, serve to explain the principles of the invention. In the drawings:

FIG. 4b illustrates the ultrasound image produced by the ultrasound probe of FIG. 4a.

DETAILED DESCRIPTION OF THE INVENTION

Reference will now be made in detail to the present embodiments of the invention, examples of which are illustrated in the accompanying drawings. Wherever possible, the same reference numbers will be used throughout the drawings to refer to the same or like parts.

Figure 1:
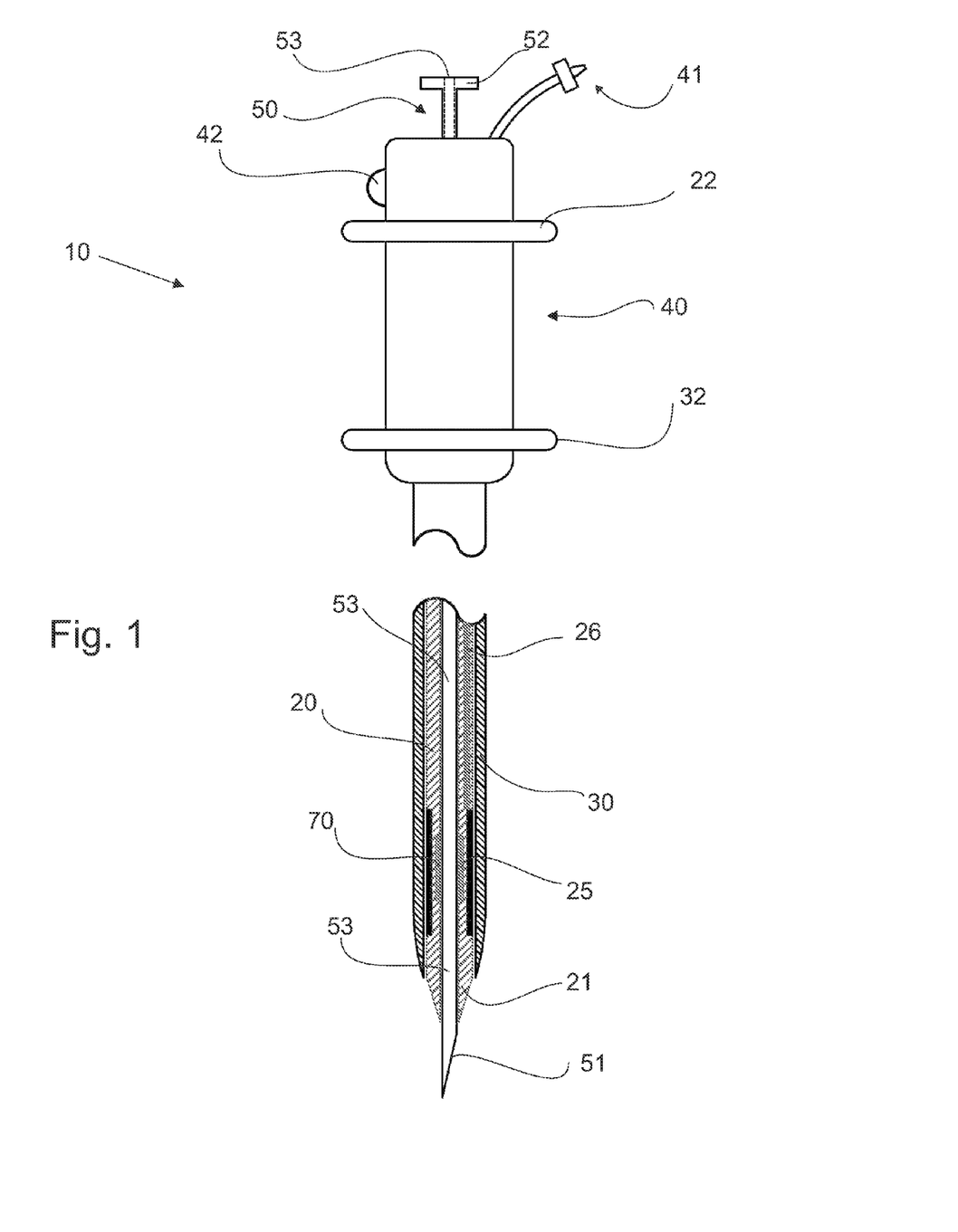
FIG. 1 illustrates a partial cross sectional side view of a fistula creation apparatus consisting with the present invention.

FIG. 1 depicts a preferred embodiment of the fistula creation device of the present invention. Device 10 is configured to be inserted by an operator through the skin of a patient to create and/or maintain a fistula that provides a flow of blood between a first vessel and a second vessel, such as a long-term flow of blood to achieve a therapeutic benefit. Device 10 includes an elongate tubular structure with a proximal end and a distal end, the tubular structure comprising multiple tubes that surround or are slidingly received within a separate tube. Each tube may have a rigid, semi-rigid, and/or flexible construction and each tube comprises one or more materials such as: nylon; polyvinyl chloride; polyethylene; polypropylene; polyimide; Pebax™; Hytrel™; polyurethane; silicone; steel; Nitinol™; blends, alloys and copolymers of the preceding, or other biocompatible materials, and may include a structural braid such as a nylon or metal braid commonly used in interventional guide catheters. Each tube may include a tapered, sharpened, beveled, expandable such as balloon expandable, and/or energy emitting distal end, and each tube may include one or more lumens, such as a Teflon-lined or Teflon-coated lumen. The elongate tubular structure may be rigid or flexible along a majority of its length, or may include both rigid and flexible portions such as two rigid portions separated by a flexible hinge portion. Device 10 further includes, on its proximal end, handle 40, which is grasped by an operator to advance, retract, rotate, control, activate, and/or otherwise manipulate device 10 or a component or sub-assembly of device 10. Each advanceable and/or retractable tube of device 10 may be attached at its proximal end to one or more advancement and/or retraction controls, such as a tube that is operably attached to a control integral to or proximate to handle 40. Handle 40 may include additional controls, such as a control to enlarge a dilator, inflate a balloon, deploy an implant, initiate energy or agent delivery, activate a diagnostic device and/or perform another function.

The outermost tube, outer sheath 30, which preferably has a tapered distal end and is constructed of a biocompatible plastic, surrounds and slidingly receives a first slidable core, inner core 20, which includes conically tapered tip 21 and is preferably constructed of biocompatible metal and/or plastic. Fistula creation assembly 25 is mounted near the distal end of inner core 20 and is configured to create a fistula on demand by an operator. Fistula creation assembly 25 may include one or more of various means to create the fistula such as a cone shaped dilator, not shown, such as a dilator that is expandable and/or configured to deliver energy. Fistula creation assembly 25 may include a force-exerting balloon, such as a compliant or non-compliant balloon and/or a balloon to dilate an implant. Alternatively or additionally, fistula creation assembly 25 may include a delivery assembly and an anastomotic implant, such as a vessel-to-vessel tensioning anastomotic clip and/or a fistula scaffolding assembly. Alternatively or additionally, fistula creation assembly 25 may include an energy delivery element such as an element configured to deliver electrical energy such as radiofrequency or microwave energy; cryogenic energy; heat; radiation; chemical energy; light; and/or other forms of energy. Energy may be delivered to ablate tissue, cut tissue and/or coagulate blood and tissue. Alternatively or additionally, fistula creation assembly 25 may include an agent delivery assembly, such as an agent delivery mechanism configured to deliver one or more of anti-proliferatives; anti-biotics; and anti-thrombogenics. In a preferred embodiment, fistula creation assembly 25 further is configured to modify an existing fistula, such as a fistula created by device 10 previously used to create the fistula, or by a separate device 10 or an alternative fistula creation device, such as during the same medical procedure or a previously performed procedure. In order to modify an existing fistula, fistula creation assembly 25 may include an anastomotic implant, such as a second anastomotic implant nested within a first implant, an expandable balloon, an energy or agent delivery element, a tissue removing element such as a forward or pull back atherectomy catheter, or other means. Other fistula modifying events can be performed such as the placement of an implant, which partially covers the fistula from either the venous or arterial side.

Referring back to FIG. 1, fistula creation assembly 25 is operably attached to conduit 26, a flexible or rigid conduit which travels proximally to handle 40. Conduit 26 may include one or more of: a power or data transfer conduit such as one or more electrical wires and/or optical fibers, a tube such as an inflation lumen or cryogenic flow tube; and a slidable cable such as a pull wire. Conduit 26 is electrically attached through an electrical switch control, button 42, to another control on handle 40, port 41. Port 41 is an electrical jack that can be attached to an energy delivery unit such as an RF generator, not shown. An operator depresses button 42 to deliver energy to fistula creation assembly 25. In an alternative or additional embodiment, port 41 is attached to a balloon endoflator that is used to inflate a balloon integral to fistula creation assembly 25. In another alternative or additional embodiment, port 41 is attached to a drug delivery pump or supply to deliver drugs to fistula creation assembly 25. Outer sheath 30 is operably attached to a control on handle 40, sheath retraction knob 32, which can be slid proximally by an operator to retract outer sheath 30 and subsequently slid distally to advance outer sheath 30. Outer sheath 30 is retracted to expose fistula creation assembly 25, such as when fistula creation assembly 25 is an expandable balloon and/or an anastomotic implant delivery assembly such as an assembly including a self-expanding anastomotic implant. In an alternative embodiment, inner core 20 is advanced to expose fistula creation assembly 25, or a combination of advancing inner core 20 and retracting outer sheath 30 is performed. Inner core 20 is operably attached to core advancement knob 22 of handle 40 such that inner core 20 can be advanced and retracted by sliding core advancement knob 22 forward or back.

Located in the distal portion of inner core 20 and in proximity to fistula creation element 25 is visualization element 70, preferably an ultrasound element such as a phased array of ultrasound crystals, signal and power wires not shown, or a rotating ultrasound crystal, rotating shaft and signal and power wires not shown. Visualization element 70 can be electrically connected to an ultrasound monitor, not shown, such that a cross sectional view of the tissue and other structures surrounding the distal portion of device 10 and fistula creation assembly 25 can be visualized. In alternative embodiments, visualization element 70 consists of a visualization marker, such as an ultrasonically reflective surface that can be visualized with an external ultrasound probe, a radiopaque marker that can be visualized under fluoroscopy, a magnetic marker, and other markers compatible with visualization equipment found in hospitals, doctor's offices and other health care settings. An operator utilizes visualization element 70 during various procedural steps involving device 10, such as penetration of its distal end through the skin and vessels of the patient and rotational orientation of the device. Visualization element 70 also provides valuable information prior to, during, and after the activation of fistula creation element 25 such as information relating to the inflation of a balloon and/or placement of an anastomotic implant. In an alternative embodiment, device 10 further includes a flow measurement element, not shown, preferably embedded in visualization element 70, such as a Doppler ultrasound function. In another alternative embodiment, a visualization catheter or flow measurement catheter is inserted in a lumen of device 10, such as within the lumen of inner core 20 in which needle assembly 50 is inserted, a separate lumen of inner core 20 not shown, or a lumen of outer sheath 30. In a preferred embodiment, device 10 further includes a visualization and/or flow measurement monitor, such as a Doppler ultrasound monitor.

A second slidable core, needle assembly 50, is slidingly received within a lumen of inner core 20. Needle assembly 50, which may be rigid or flexible along its length, is preferably constructed of one or more metals such as stainless steel and Nitinol. Needle assembly 50 can be retracted, and completely removed from the lumen of inner core 20 by retraction of yet another control of handle 40, needle retraction knob 52. In an alternative embodiment, full removal of needle assembly 50 is prevented by the inclusion of one or more mechanical stops. Needle assembly 50 has a sharpened distal tip 51, which is preferably sharp and beveled. Needle assembly 50 includes a lumen from its proximal end to its distal end, guidewire lumen 53, which is configured to allow a standard interventional guidewire to be advanced therethrough, and further configured to allow needle assembly 50 to be removed leaving the previously inserted guidewire to reside within the lumen of inner core 20 previously inhabited by needle assembly 50. In an alternative embodiment, needle tip 51 may be configured to deliver energy, such as RF energy used to assist in advancement, and/or to cauterize, cut and ablate tissue.

In a preferred embodiment, a kit is provided for the creation of multiple fistulas, in a single patient or multiple patients, includes multiple fistula creation devices of FIG. 1 with varied fistula creation elements in each device. An operator selects a specific fistula creation device based on the configuration of the fistula creation element included in that device. In one alternative, a first fistula creation device creates a fistula with a different geometry than a second fistula creation device, such as might be chosen to differentiate a fistula between vessels with a first set of luminal diameters and a second set of fistulas with different luminal diameters. Numerous fistula creation parameters can be varied between a first fistula creation device and a second fistula creation device such as use of energy, fistula diameter, fistula cross section geometry such as circular cross section versus elliptical cross section wherein the major diameter of the ellipse is at least 20 percent larger than the minor diameter of the ellipse. In a preferred embodiment, the major diameter of the fistula is at least twice the minor diameter. In another preferred embodiment, a kit includes a first fistula creation device with a target fistula cross section dimensions having unequal major and minor axes, and a second fistula creation device with a target fistula cross section dimensions have similar minor axis length and greater major axis length. In a preferred method, an operator selects either the first fistula creation device or the second fistula creation device based on a visualization procedure performed on the anatomy of the patient proximate the intended fistula creation site.

Figure 2A:
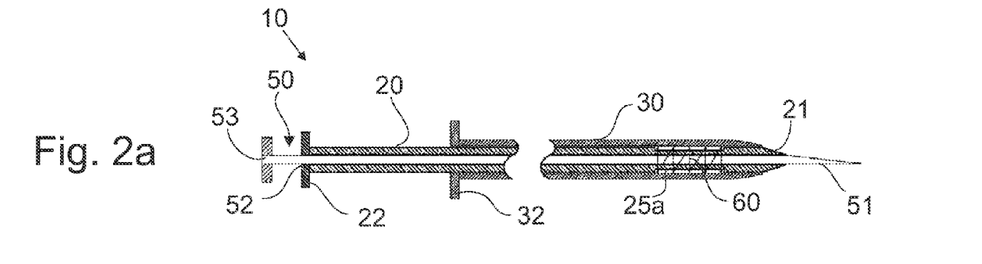
FIG. 2a illustrates a cross sectional side view of a fistula creation apparatus consistent with the present invention shown with a slidable needle assembly in the advanced position.

Referring now to FIGS. 2a through 2d, a preferred embodiment of a fistula creation device of the present invention is shown in various stages of a preferred method of activation. Referring specifically to FIG. 2a, device 10 is configured to be inserted by an operator through the skin of a patient to create and/or maintain a fistula that provides a flow of blood between a first vessel and a second vessel, such as a long-term flow of blood to achieve a therapeutic benefit. Device 10 includes an elongate tubular structure with a proximal end and a distal end, the tubular structure comprising multiple tubes that surround or are slidingly received within a separate tube. Each tube may have a rigid, semi-rigid, and/or flexible construction and each tube comprises one or more materials such as: nylon; polyvinyl chloride; polyethylene; polypropylene; polyimide; Pebax™; Hytrel™; polyurethane; silicone; steel; Nitinol™; blends, alloys and copolymers of the preceding, or other biocompatible materials, and may include a structural braid such as a nylon or metal braid commonly used in interventional guide catheters.

The outermost tube, outer sheath 30, which preferably has a tapered distal end, surrounds and slidingly receives a first slidable core, inner core 20, which includes conically tapered tip 21. Outer sheath 30 includes on its proximal end sheath advancement knob 32, which is manipulated by an operator to advance and retract outer sheath 30. Inner core 20 includes on its proximal end, core advancement knob 22, which is manipulated by an operator to advance and retract inner core 20. Balloon 25 is mounted near the distal end of inner core 20 and is expandable on demand by an operator, inflation lumen and endoflator attachment port not shown, such as to create the fistula and/or expand an implant placed to maintain the fistula. Balloon 25 may comprise a compliant or non-compliant balloon. Surrounding balloon 25 is an anastomotic implant, clip 60, which is deployed in the fistula to perform one or more functions including but not limited to: scaffolding an opening between the first vessel and the second vessel; reducing neointimal proliferation into the fistula flow path; preventing tissue from protruding into the fistula flow path; placing a portion of the first vessel wall in tension with the tissue of the second vessel wall; and reducing bleeding of the tissue neighboring the fistula; enhancing healing of the tissue neighboring the fistula. In a preferred embodiment, the anastomotic implant includes an active agent, such as an antithrombogenic or anti-proliferative agent, and may also include a covering or partial covering.

A second slidable core, needle assembly 50, is slidingly received within a lumen of inner core 20. Needle assembly 50, which may be rigid or flexible along its length, is preferably constructed of one or more metals such as stainless steel and Nitinol. Needle assembly 50 can be retracted, and completely removed from the lumen of inner core 20 by retraction of needle retraction knob 52. In a preferred embodiment, Inner core 20 can also be retracted, and completely removed from the lumen of outer sheath 30, by retraction of knob 20. Needle assembly 50 has a sharpened distal tip 51, which is preferably sharp and beveled. Needle assembly 50 includes a lumen from its proximal end to its distal end, guidewire lumen 53, which is configured to allow a standard interventional guidewire to be advanced therethrough, and further configured to allow needle assembly 50 to be removed leaving the previously inserted guidewire to reside within the lumen of inner core 20 previously inhabited by needle assembly 50. In an alternative embodiment, needle assembly 50 is partially retracted but remains within lumen of inner core 20. In another alternative embodiment, needle tip 51 may be configured to deliver energy, such as RF energy used to assist in advancement, and/or to cauterize, cut and ablate tissue. In a preferred method, device 10 is advanced through the skin, through a first vessel and into the lumen of a second vessel with needle assembly 50 in the fully advanced position. A locking mechanism, not shown, may be engaged to prevent relative motion between needle assembly 50 and outer sheath 30 during insertion and subsequent advancement. A guidewire is then advanced through guidewire lumen 53 and further advanced down the lumen of the second vessel.

Figure 2B:
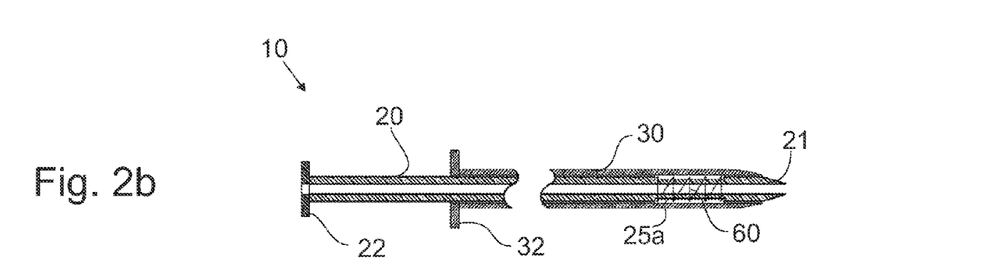
FIG. 2b illustrates the fistula creation apparatus of FIG. 2a with the needle assembly removed.
Figure 2C:
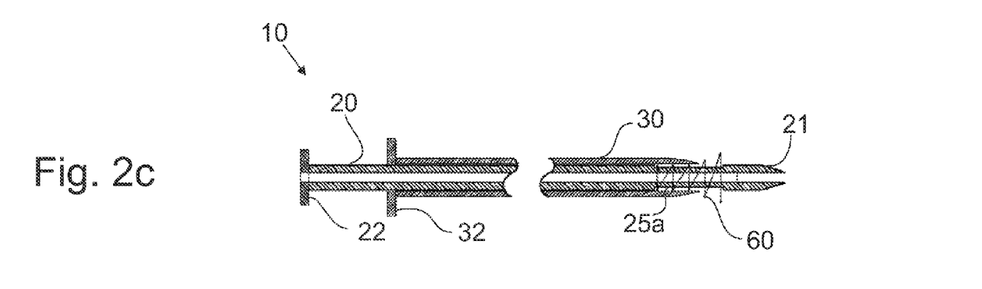
FIG. 2c illustrates the fistula creation apparatus of FIG. 2b with an outer sheath retracted such that an integral anastomotic implant is partially expanded.
Figure 2D:
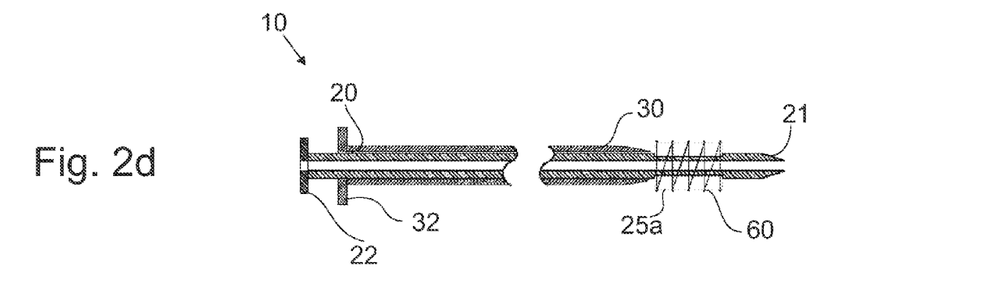
FIG. 2d illustrates the fistula creation apparatus of FIG. 2c with the outer sheath further retracted such that the integral anastomotic implant is fully expanded.

Referring now to FIG. 2b, needle assembly 50 has been completely removed from the lumen of inner core 20, such as when a guidewire has been successfully placed from a location outside the patient's skin to and into the second vessel. Referring now to FIG. 2c, the distal end of clip 60 has been released from being constrained by outer sheath 30, either by retraction of outer sheath 30, advancement of inner core 20, or a combination of both movements. Clip 60 of FIGS. 2a through 2d is self-expanding, such as a resiliently biased tubular structure made of Nitinol. In FIG. 2d, clip 60 has been fully released from being constrained and is in a fully expanded condition. Balloon 25 has been inflated, inflation lumen and endoflator attachment not shown, to provide additional expansion force to clip 60. In an alternative embodiment, clip 60 is plastically deformable, or includes plastically deformable portions, such that balloon 25 is required to expand clip 60. In a preferred embodiment, device 10 of FIGS. 2a through 2d is used as a system in conjunction with one or more additional devices to create and/or maintain the fistula. Such additional devices include but are not limited to guidewires and various over-the-wire devices that are placed over the guidewire placed through needle assembly 50, after needle assembly 50 is removed. These additional over-the-wire devices may be placed within a lumen of inner core 20, within a lumen of outer sheath 30 with inner core 20 removed, or over the guidewire after device 10 has been completely removed. These over-the-wire devices include but are not limited to: balloon catheters; anastomotic implant delivery devices and implants; flow measurement catheters; angiography catheters; venography catheters; and other over-the wire devices applicable to modifying the fistula, such as modifying the flow of the fistula, or to perform a procedure to otherwise enhance and/or maintain the long term benefit of the fistula.

Referring now to FIGS. 3a through 3f, a preferred method of using the fistula creation device of the present invention is shown. A cross sectional view of a patient's anatomy at a proposed fistula location 111 is depicted wherein artery 130 is directly above vein 120 in relation to skin surface 105. Intended fistula location 111 may be determined using one or more visualization techniques including but not limited to: angiography; venography; extra-vascular ultrasound; intravascular ultrasound; and MRI. Intended fistula location 111 may be determined using one or more flow measurement techniques such as Doppler ultrasound. The intended fistula location 111 may be selected based on parameters selected from the group consisting of: first vessel diameter; second vessel diameter; artery diameter; vein diameter; ratio of artery to vein diameter; distance between the artery and vein lumens; geometric relationship between the artery and vein lumens; distance from an arterial side branch; distance from an venous side branch; arterial flow; venous flow; oxygen content in artery; oxygen content in vein; wall thickness of artery; wall thickness of vein; degree of calcification of artery; degree of calcification of vein; geometric relationship between the artery and vein lumens at the fistula site; hemodynamic factors; other parameters; and combinations thereof.

Figure 3A:
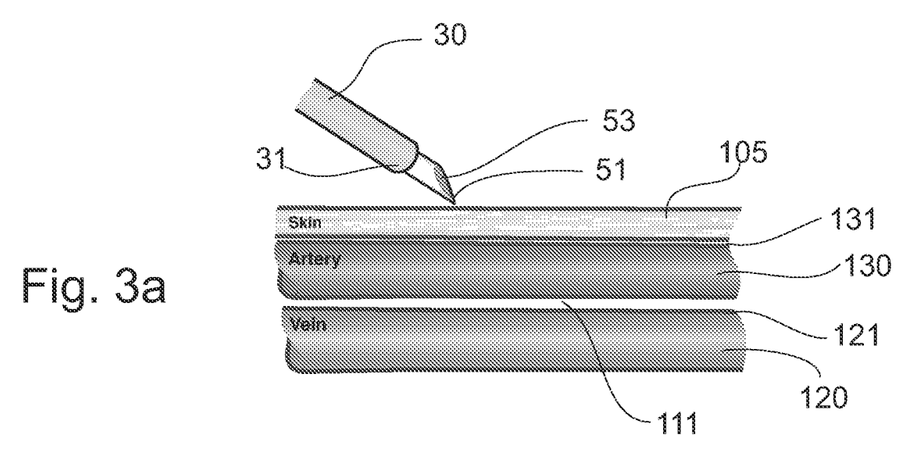
FIG. 3a is a cross sectional side view of a device and method for creating a fistula consistent with the present invention shown prior to advancement of the device through the patient's skin.

Artery 130 includes, in closest proximity to skin 105, arterial wall 131. Vein 120 includes, in closest proximity to artery 130, venous wall 121. At the intended fistula location 111 of the patient, the vessels may lie in various geometric configurations, such as the geometry of FIGS. 3a through 3f wherein the first vessel is relatively "on top" of the second vessel such that the lumen of the first vessel lies relatively proximate the shortest line between the lumen of the second vessel at the fistula location and the surface of the patient's skin. In alternative fistula locations, the vessels may lie in a more "side-to-side" configuration. When inserted, the elongate body of outer sheath 30 is positioned to lie relatively in the plane defined by the lumens of the two vessels near the intended fistula location. While maintaining position within this plane, the fistula creation device can be inserted at an angle relatively perpendicular to the surface of the patient's skin, or at a smaller angle as is shown in FIG. 3a, such as an angle between 20 and 80 degrees. This insertion angle may be chosen by the clinician to form the resultant fistula angular geometry between the two vessels, such as at a small insertion angle to correspond to a similarly small angle between the lumen of the first vessel and the lumen of the fistula. Such a small angle between the first vessel lumen and the fistula lumen may be desirous to reduce turbulent flow through the fistula. In alternative embodiments, an insertion angle approximating ninety degrees may be chosen, such as to minimize the length of the resultant fistula. Vein 120 is preferably a vein located in a limb of the patient, such as a vein selected from the group consisting of: saphenous vein; femoral vein; iliac vein; popliteal vein; brachial vein; basilic vein; cephalic vein; medial forearm vein; medial cubital vein; axillary vein; and jugular vein. Artery 130 is preferably an artery in a limb of the patient, such as an artery selected from the group consisting of: axillary artery; brachial artery; ulnar artery; radial artery; profundal artery; femoral artery; iliac artery; popliteal artery; carotid artery.

Referring now specifically to FIG. 3a, a fistula creation device is positioned with its distal end near an intended skin puncture site and includes outer sheath 30 with distal end 31. Outer sheath 30 is preferably constructed of a biocompatible catheter material, such materials and construction methods described in detail hereabove. Extending beyond distal end 31 is the distal end of a slidable needle assembly including needle tip 51 and guidewire lumen 53. The needle assembly is preferably constructed of a metal or metal alloy such as stainless steel or Nitinol, and needle tip 51 is a sharpened, beveled tip.

Figure 3B:
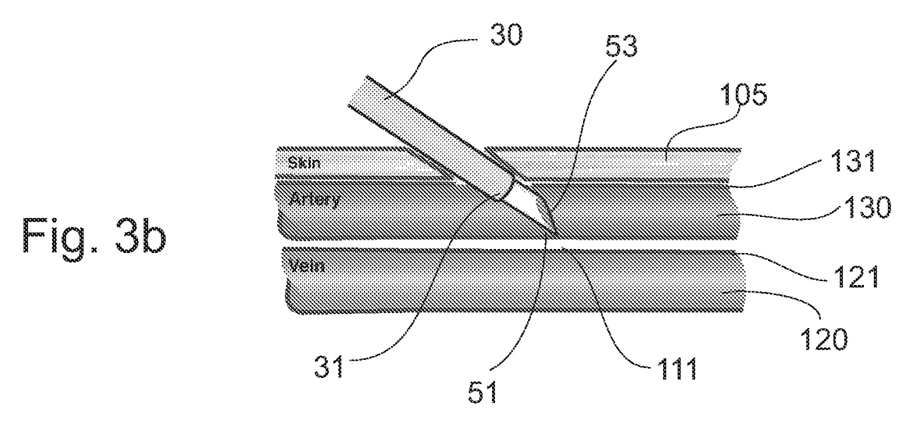
FIG. 3b illustrates the device and method of FIG. 3a shown with the distal end of a slidable needle assembly of the device having penetrated the skin and the first wall of an artery.
Figure 3C:
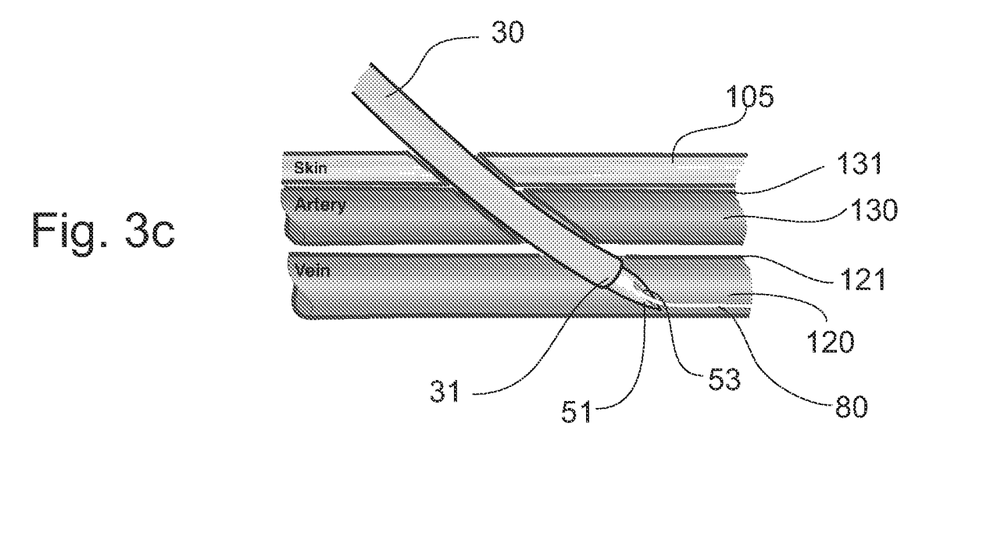
FIG. 3c illustrates the device and method of FIG. 3b shown with the needle assembly having further penetrated a second wall of the artery and a first wall of a vein, and a guidewire having been advanced down the vein through a lumen of the needle assembly.
Figure 3D:
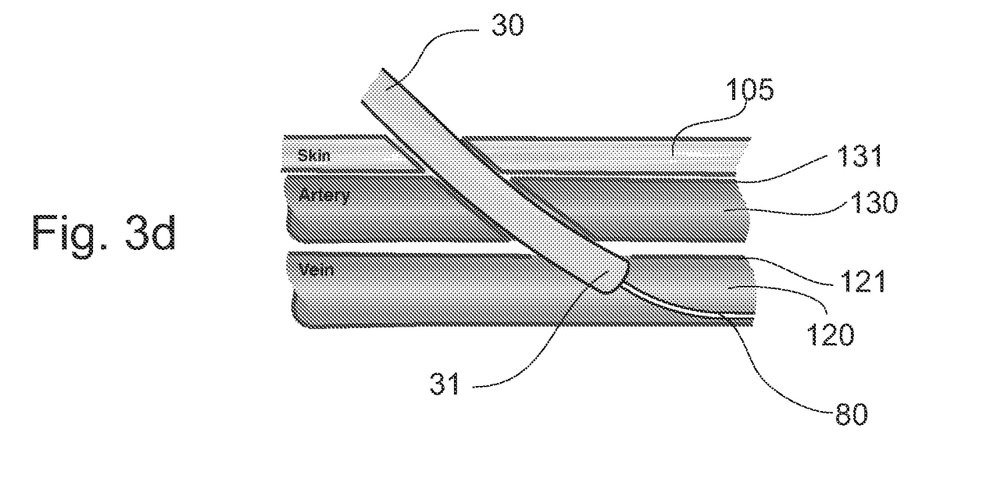
FIG. 3d illustrates the device and method of FIG. 3c shown with the needle assembly having been retracted while leaving the guidewire seated in the vein.

Referring now to FIG. 3b, needle tip 51 has been advanced through skin 105, through artery wall 31, and into the lumen of artery 130. Distal end 31 of outer sheath 30 has also passed through skin 105 without any significant displacement between needle tip 51 and distal end 31, either by a releasable fixation device, not shown but integral to the fistula creation device, or by stabilization of both the outer sheath 30 and the needle assembly by the operator. Referring now to FIG. 3c, needle tip 51 has been advanced out of artery 130, through venous wall 121 and into the lumen of vein 120. Similar to the advancement shown in FIG. 3b, there has been no relative displacement between needle tip 51 and distal end 31 of outer sheath 30, such that distal end 31 has also advanced into the lumen of vein 120. Guidewire 80 has been advanced from the proximal end of the fistula creation device, through guidewire lumen 53 and down the lumen of vein 120. Referring now to FIG. 3d, the needle assembly has been retracted such needle tip 51 has moved proximal to outer sheath 30 distal end 31, while leaving guidewire 80 deep seated into vein 120.

Figure 3E:
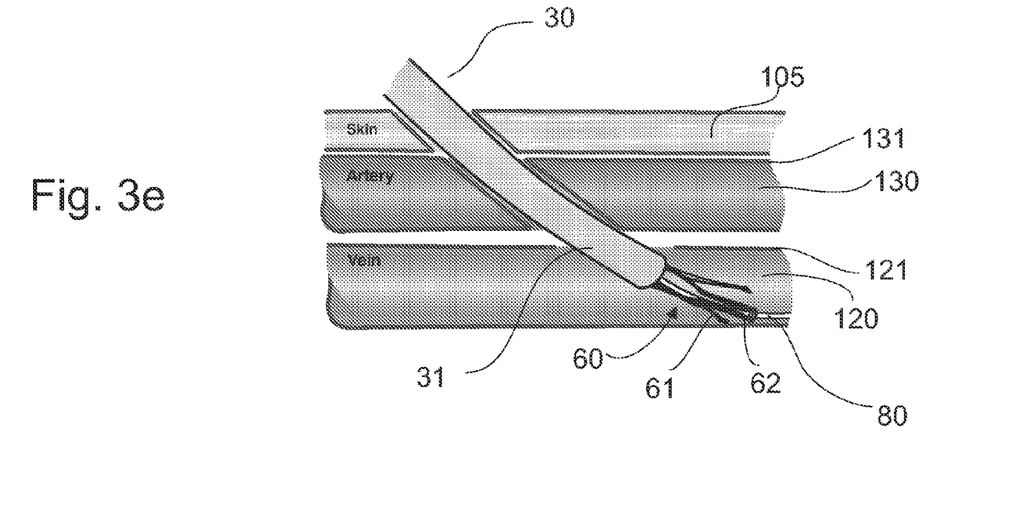
FIG. 3e illustrates the device and method of FIG. 3d shown with an anastomotic implant of the device partially deployed in the vein.
Figure 3F:
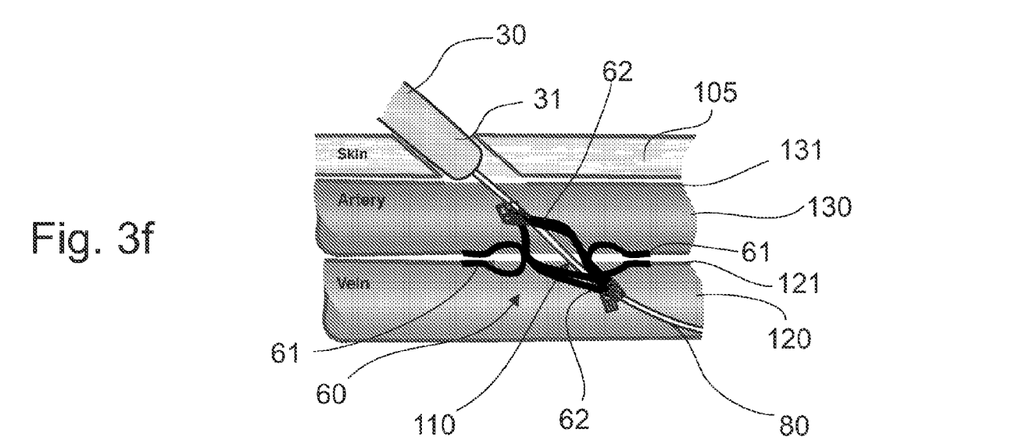
FIG. 3f illustrates the device and method of FIG. 3e shown with the anastomotic implant of the device fully deployed in the fistula between the artery and the vein, and the device outer sheath partially retracted from the patient.

Referring now to FIG. 3e, a self-expanding anastomotic implant, clip 60, is partially deployed out of distal end 31 of outer sheath 30, such that two tensioning arms 61 and two stabilizing arms 62 have been released from being constrained within outer sheath 30. Clip 60 has been partially deployed through one or more actions including: pushing clip 60 out of outer sheath 30 via advancement of a core contained within outer sheath 30; retracting sheath 30 such as while maintaining the longitudinal position of clip 60; or by a combination of these two actions. While clip 60 is partially deployed, the fistula creation device is retracted to a position wherein one or more of tensioning arms 61 are in firm contact with venous wall 121, position not shown. Clip 60 is then fully deployed such as by retraction of sheath 30, advancement of clip 60, or a combination of the two actions. Referring now to FIG. 3f, clip 60 has been fully deployed such that fistula 110 is scaffolded by clip 60, the four tensioning arms 61 placing vein 120 and artery 130 in tension at a location neighboring fistula 110, and stabilization arms 62 stabilizing clip 60 in the vessels to prevent twisting or other clip 60 migrations. Clip 60 is preferably configured such that fistula 110 has an oval cross-section, with a major axis at least twenty percent greater than the minor axis of the oval. In a preferred embodiment, the major axis has a diameter larger than either vein 120 or artery 130's luminal diameter. In an alternative embodiment, clip 60's construction geometry causes fistula 110 to have a circular cross section.

Shown in FIG. 3f, the fistula creation device is being withdrawn, such that distal end 31 of outer sheath 30 is almost removed from entering skin 105. Guidewire 80 remains in place, such that one or more additional devices can be placed over-the-wire and easily access either the artery 130 or venous 120 side of fistula 110. These subsequent over-the-wire devices, described in detail in reference to FIG. 2d, can be used to assess the fistula such as an ultrasound catheter to visualize the fistula, or a Doppler ultrasound catheter to measure fistula flow. The over-the-wire devices can be used to modify the fistula such as to modify the flow rate through the fistula, or to otherwise improve the therapeutic benefit of the fistula such as to increase the long-term patency of the fistula or to minimize adverse side effects of the fistula. In a preferred embodiment, an over-the-wire or other procedure is performed to measure flow through the fistula. If inadequate flow is determined, a flow modification procedure may be performed, such as an over-the-wire flow modification procedure utilizing an inflatable balloon or a tissue removing device to increase fistula flow. In a preferred embodiment, the inflatable balloon has a non-circular geometry which corresponds to a fistula created with a non-circular geometry. The balloon may be integral to the fistula creation device, or a separate over-the-wire catheter, and may be inflated to apply force to clip 60, or a second implant, all not shown. Other flow modification procedure may also be performed, such as procedures which place implants, within or external to the flow path, to increase or decrease fistula flow to maximize therapeutic benefit and/or reduce adverse side effects. Other flow modification procedures that may be performed include application of an agent such as an anti-biotic, anti-thrombogenic or anti-proliferative agent, or delivery of energy such as radiation delivery to prevent neointimal growth.

The method and device of FIGS. 3a through 3f are used to create a fistula for therapeutic benefit such as to treat a patient with COPD. The fistula can be created for various purposes such as: increasing the oxygen content of venous blood supplying a lung of the patient, increase the oxygen content of arterial blood; and/or decreasing systemic vascular resistance. The fistula can be created for an acute period less than twenty-four hours, a sub-chronic period between twenty-four hours and thirty days, as well as for a chronic period longer than thirty days. The fistula preferably provides a flow of blood from the arterial system to the venous system of greater than 5 ml/min, typically greater than 50 ml/min. Clip 60 provides one or more functions including but not limited to: scaffolding an opening between the first vessel and the second vessel; reducing neointimal proliferation into the fistula flow path; preventing tissue from protruding into the fistula flow path; placing a portion of the first vessel wall in tension with the tissue of the second vessel wall; reducing bleeding of the tissue neighboring the fistula; enhancing healing of the tissue neighboring the fistula; and combinations thereof. While clip 60 has been described as a self-expanding device such as a resiliently biased Nitinol component, anastomotic implants that are plastically deformable or include both self-expanding sections and balloon expandable portions are also preferred. In an alternative embodiment, clip 60 includes a covering, such as a covering that surrounds the interior of the tissue within the fistula between the artery and vein lumens. The covering is a biocompatible material such as polytetrafluoroethylene; Dacron; Nitinol; stainless steel; or combinations thereof. In another alternative embodiment, clip 60 includes an agent, such as an agent that is eluded over time including anti-bacterial, anti-thrombogenic and/or anti-prolific agents. While, the method of FIGS. 3a through 3f illustrate an artery to vein connection method, a vein to artery approach is also a preferred method of this invention.

The device and method of FIGS. 3a through 3f create an initial puncture through the skin of the patient, subsequently penetrating into and through the first vessel, and into the lumen of the second vessel. In an alternative, also preferred embodiment, not shown, a standard vessel introducer and sheath is utilized, making the initial puncture through the skin of the patient and into the first vessel. The fistula creation device distal end is then inserted into the sheath, passing through the skin and into the first vessel. The fistula creation device distal end exits the end of the sheath and further exits the lumen of the first vessel at the intended fistula location site by penetrating through the first vessel wall, and enters the lumen of the second vessel by penetrating through the second vessel wall. The intended fistula location may be proximate the site that the vessel introducer entered the first vessel, or at a location remote from this site, such as at a location greater than 20 mm from the first vessel entry site. Fistulas may be created remote from the first vessel entry site by intraluminally advancing the introducer sheath and/or the fistula creation device down the lumen of the first vessel prior to the distal end of the fistula creation device exiting the first vessel lumen and penetrating into the second vessel.

Figure 4A:
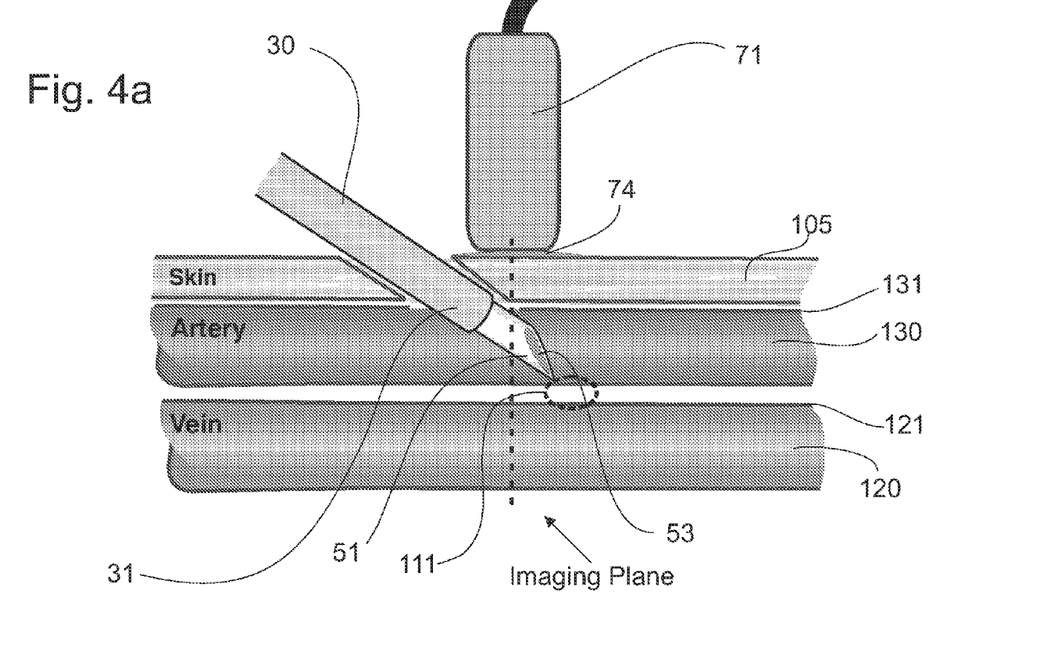
FIG. 4a is a cross sectional side view of a device and method for creating a fistula consistent with the present invention shown with advancement of the distal end of the device through the patient's skin and into an artery and an ultrasound probe located proximate the entry site.
Figure 4B:
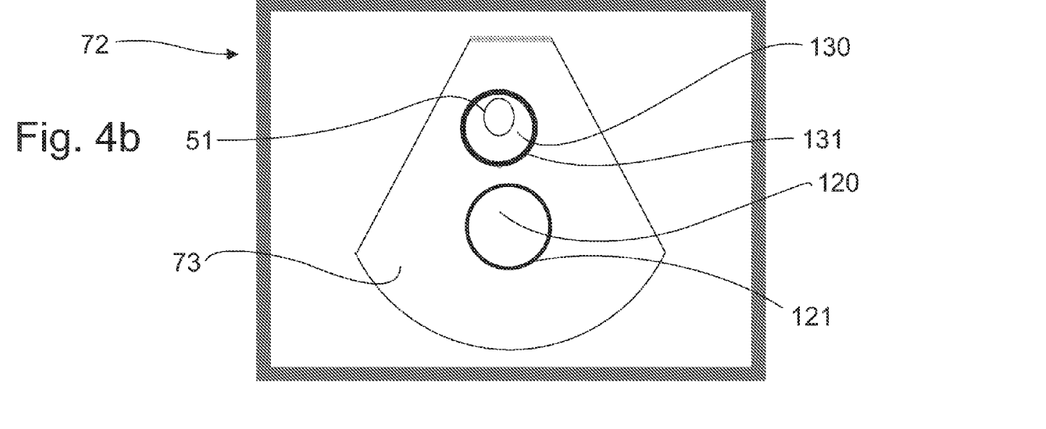

Referring now to FIGS. 4a and 4b, a method and system for creating a fistula is shown in which an operator utilizes a fistula creation device and ultrasound visualization system in combination. A cross sectional view of a patient's anatomy at a proposed fistula location 111 is depicted wherein artery 130 is directly above vein 120 in relation to skin surface 105. Intended fistula location 111 may be determined using one or more visualization techniques including but not limited to: angiography; venography; extra-vascular ultrasound; intravascular ultrasound; and MRI. Intended fistula location 111 may be determined using one or more flow measurement techniques such as Doppler ultrasound. The intended fistula location 111 may be selected based on parameters selected from the group consisting of: first vessel diameter; second vessel diameter; artery diameter; vein diameter; ratio of artery to vein diameter; distance between the artery and vein lumens; geometric relationship between the artery and vein lumens; distance from an arterial side branch; distance from an venous side branch; arterial flow; venous flow; oxygen content in artery; oxygen content in vein; wall thickness of artery; wall thickness of vein; degree of calcification of artery; degree of calcification of vein; geometric relationship between the artery and vein lumens at the fistula site; hemodynamic factors; other parameters; and combinations thereof.

Artery 130 includes, in closest proximity to skin 105, arterial wall 131. Vein 120 includes, in closest proximity to artery 130, venous wall 121. While vein 120 and artery 130 are shown in a line relatively perpendicular to skin 105, adjusting the orientation of outer sheath 30 can not only vary insertion angles, but also accommodate anatomies with vessels in a relatively side-by-side configuration (relatively equidistant from skin surface 105) as has been described hereabove in reference to FIGS. 3a through 3f. In a preferred method, the fistula creation device enters the skin at an angle relatively perpendicular to skin 105. In another preferred embodiment, the fistula creation device penetrated the skin at an angle between 20 and 80 degrees relative to the surface of the skin 105. Vein 120 is preferably a vein located in a limb of the patient, such as a vein selected from the group consisting of: saphenous vein; femoral vein; iliac vein; popliteal vein; brachial vein; basilic vein; cephalic vein; medial forearm vein; medial cubital vein; axillary vein; and jugular vein. Artery 130 is preferably an artery in a limb of the patient, such as an artery selected from the group consisting of: axillary artery; brachial artery; ulnar artery; radial artery; profundal artery; femoral artery; iliac artery; popliteal artery; carotid artery.

Referring now to specifically to FIG. 4a, a fistula creation device is positioned with its distal end at an intended fistula site 111. The fistula creation device includes outer sheath 30, which is preferably constructed of a biocompatible catheter material, such materials and construction methods described in detail hereabove. Extending beyond distal end 31 of outer sheath 30 is the distal end of a slidable needle assembly including needle tip 51 and guidewire lumen 53. The needle assembly is preferably constructed of a metal or metal alloy such as stainless steel or Nitinol, and needle tip 51 is a sharpened, beveled tip. Needle tip 51 has been advanced through skin 105, through artery wall 31, and into the lumen of artery 130 residing near intended fistula site 111. Distal end 31 of outer sheath 30 has also passed through skin 105 without any significant displacement between needle tip 51 and distal end 31, either by a releasable fixation device, not shown but integral to the fistula creation device, or by stabilization of both the outer sheath 30 and the needle assembly by the operator.

Also shown in FIG. 4a is ultrasound probe 71, which is positioned relatively orthogonal to the surface of skin 105, and preferably held by an operator, operator not shown, to provide a visual cross sectional image of intended fistula site 111, as well as artery 130, vein 120, and any devices crossing through the imaging plane of ultrasound probe 71. Ultrasonic coupling gel 74, common to external ultrasound probe use, is first placed on the skin, in the area to be visualized, to enhance the image produced by ultrasound probe 71 via improved acoustic coupling between ultrasound probe 71 and skin 105. Referring additionally to FIG. 4b, ultrasound probe 71 is attached to an ultrasound generator, not shown, as well as ultrasound monitor 72 which displays on imaging area 73 the cross sectional image associated with the imaging plane of FIG. 4a. Manipulation of probe 71, either in the position of contact with skin 105 and/or the relative angle made with the surface of skin 105, modifies the location of the imaging plane and the associated image displayed on monitor 72. Ultrasound probe 71 and monitor 72 are used and manipulated by an operator as a system including the fistula creation device of the present invention. This system is used to assess and pre-determine the location of intended fistula location 111. The visualization equipment is also used to view and confirm advancements of the percutaneous devices such as catheter, sheath, inner tube and guidewire advancements; confirm device locations such as device distal end (tip) locations; and assist in other preferred fistula creation steps of the present invention in which real-time visualization of the procedure can be made available to an operator. In an alternative, also preferred embodiment, as an alternative to or in conjunction with ultrasound probe 71, an internal ultrasound probe provides an image to monitor 72. The internal probe, not shown, is selected from the group consisting of: an ultrasound catheter such as a rotational or phased array intravascular ultrasound catheter; an inserted probe such as a transesophageal probe; and combinations thereof.

In subsequent steps, not shown but similar to steps 3c through 3f hereabove, needle tip 51 will be advanced out of artery 130, through venous wall 121 and into the lumen of vein 120. A guidewire, not shown, will be advanced from the proximal end of the fistula creation device, through guidewire lumen 53 and down the lumen of vein 120. The needle assembly will then be retracted such that needle tip 51 will be retracted proximal to distal end 31 of outer sheath 30, while leaving the guidewire deep seated into vein 120. An anastomotic implant, not shown, is deployed such as by retraction of sheath 30 while maintaining the position of the anastomotic implant. The anastomotic implant is configured such that the resultant fistula has an oval cross-section, with a major axis at least twenty percent greater than the minor axis of the oval. The fistula creation device is then withdrawn, such that distal end 31 of outer sheath 30 is almost removed from entering skin 105. The guidewire preferably remains in place, such as through a standard vessel introducer, not shown. In a preferred embodiment, outer sheath 30 performs as the vessel introducer. Leaving the guidewire in place allows one or more additional devices to be placed over-the-wire and easily access either the venous or arterial side of the fistula. These subsequent over-the-wire devices, described in detail in reference to FIG. 2d, can be used to assess the fistula such as an ultrasound catheter to visualize the fistula, or a Doppler ultrasound catheter to measure fistula flow. The over-the-wire devices can be used to modify the fistula such as to modify the flow rate through the fistula, or to otherwise improve the therapeutic benefit of the fistula such as to increase the long-term patency of the fistula or to minimize adverse side effects of the fistula. In a preferred embodiment, an over-the-wire or other procedure is performed to measure flow through the fistula. If inadequate flow is determined, a flow modification procedure may be performed, such as an over-the-wire flow modification procedure utilizing an inflatable balloon or a tissue-removing device to increase fistula flow. In a preferred embodiment, the inflatable balloon has a non-circular geometry that corresponds to a fistula created with a non-circular geometry. The balloon may be integral to the fistula creation device, or a separate over-the-wire catheter, and may be inflated to apply force to clip 60, or a second implant, all not shown. Other flow modification procedure may also be performed, such as procedures that place implants, within or external to the flow path, to increase or decrease fistula flow to maximize therapeutic benefit and/or reduce adverse side effects.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A device for creating a fistula in a patient comprising:
an elongate tubular structure having a proximal end and a distal end, wherein the distal end is configured to pass first through the skin of the patient, then through a first vessel, and then into a second vessel, wherein said elongate tubular structure includes an outer tube and a slid- able core slidingly received by said outer tube, wherein the slidable core has a proximal end, a distal end, and a lumen therethrough;

a self-expanding fistula creation assembly disposed near the distal end of the elongate tubular structure, said self-expanding fistula creation assembly being adapted to create and maintain a fistula that provides a flow of blood between the first vessel and the second vessel; and a needle removably received in a lumen of the slidable core, wherein the needle has a needle tip that extends beyond the distal end of the elongate tubular structure to penetrate skin and the first and second vessels as the elongate tubular structure is advanced;

wherein the self-expanding fistula creation assembly is carried on the first slidable core and constrained by the tubular structure such that the outer tube can be retracted to release the self-expanding fistula creation assembly in the penetration.

2. The device of claim 1, wherein the slidable core has a tapered or beveled distal end.

3. The device of claim 1, wherein the device is configured to be advanced and/or retracted over a guidewire contained within a lumen of the needle.

4. The device of claim 1, wherein the fistula creation assembly comprises one or more of a cone shaped dilator, an expandable assembly such as a balloon, an energy delivery element, an agent delivery element, and an anastomotic implant.

5. The device of claim 1, wherein the self-expanding fistula creation assembly comprises an anastomotic implant constructed of materials selected from the group consisting of stainless steel or Nitinol, plastically deformable materials, and combinations thereof.

6. The device of claim 5, wherein the fistula creation assembly further comprises an expandable balloon configured to apply radial force to at least a portion of the anastomotic implant, said radial force applied to said anastomotic implant during deployment of the anastomotic implant in the fistula and/or after the deployment of the anastomotic implant in the fistula.

7. The device of claim 5, wherein the anastomotic implant is configured to perform one or more of the following functions apply a radial force to the fistula, apply a compressive force to the first and second vessels, and cause the flow in the fistula to tend toward laminar flow.

8. The device of claim 1, wherein the fistula is configured to: provide a therapy for chronic obstructive pulmonary disease, increase venous oxygen level, increase arterial oxygen level, decrease systemic vascular resistance, and combinations thereof.

9. The device of claim 1, further comprising a handle on the proximal end and at least one slidable core; wherein the handle includes one or more controls configured to perform one or more of the following functions:

activate or otherwise control at least a portion of the fistula creation assembly such as by controlling one or more of:
expansion of a balloon deployment of an anastomotic implant;
apply force to an anastomotic implant;
delivery of energy;
delivery of an agent such as a drug; and
advance or retract the slidable core; and combinations thereof.

10. The device of claim 1, wherein the first vessel is selected from the group consisting of axillary artery, brachial artery, ulnar artery, radial artery, profundal artery, femoral artery, iliac artery, popliteal artery, carotid artery, saphenous vein, femoral vein, iliac vein, popliteal vein, brachial vein, basilic vein, cephalic vein, medial forearm vein, medial cubital vein, axillary vein, and jugular vein.

11. The device of claim 1, wherein the second vessel wall is within 20 mm of the first vessel wall.

12. The device of claim 1, wherein the elongate tubular structure includes a lumen from its proximal end to its distal end, wherein the device is configured to reside in the patient with a guidewire in said lumen, said device further configured to be withdrawn from the patient leaving the guidewire to remain passing through the skin and into the patient, through the first vessel, through the fistula, and into the second vessel.

13. The device of claim 1, wherein the tubular structure includes a flow measurement element configured to measure flow of the patient's blood.

14. The device of claim 1, further comprising flow adjustment means, said flow adjustment means comprising one or more of:
an inflatable balloon; and
a deployable implant such as an implant deployed within the fistula, and implant configured to be deployed within a pre-existing implant, an implant which impedes flow in the fistula, and/or an implant which enlarges the fistula.

15. A system for creating a fistula comprising the device of claim 1, and an ultrasound visualization monitor.

16. A system for creating a fistula comprising:
the device of claim 1, and an apparatus selected from the group consisting of:
a balloon catheter, an anastomotic implant deployment catheter, a flow measurement device such as a flow catheter or an external Doppler probe, an angiography catheter, a venography catheter, a guidewire, an introducer, a biopsy needle, and combinations thereof.

* * * * *